(12) United States Patent
Nakagawa

(10) Patent No.: US 6,945,091 B2
(45) Date of Patent: Sep. 20, 2005

(54) GAS SENSOR HAVING IMPROVED STRUCTURE FOR INSTALLATION OF PROTECTIVE COVER

(75) Inventor: Kazuya Nakagawa, Kariya (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/737,826

(22) Filed: Dec. 18, 2003

(65) Prior Publication Data

US 2004/0124081 A1 Jul. 1, 2004

(30) Foreign Application Priority Data

Dec. 20, 2002 (JP) .......................................... 2002-370188

(51) Int. Cl.⁷ ............................................... G01N 27/26
(52) U.S. Cl. ...................... 73/31.05; 73/23.31; 204/424; 204/428
(58) Field of Search ............................. 73/23.2, 23.31, 73/31.05; 204/424, 428

(56) References Cited

U.S. PATENT DOCUMENTS

| | | | |
|---|---|---|---|
| 4,019,974 A | * | 4/1977 | Weyl et al. ................. 204/428 |
| 4,159,234 A | * | 6/1979 | Eifler et al. ................. 204/428 |
| 4,502,939 A | * | 3/1985 | Holfelder et al. ........... 204/429 |
| 4,535,316 A | * | 8/1985 | Wertheimer et al. .......... 338/34 |
| 4,818,364 A | * | 4/1989 | Weber et al. ............... 204/427 |
| 4,842,713 A | * | 6/1989 | Stahl ......................... 204/428 |
| 6,214,186 B1 | | 4/2001 | Watanabe et al. ........... 204/428 |
| 2003/0188967 A1 | * | 10/2003 | Isitani et al. ................ 204/406 |
| 2004/0050695 A1 | * | 3/2004 | Haraguchi et al. .......... 204/424 |

FOREIGN PATENT DOCUMENTS

| | | |
|---|---|---|
| EP | 0962766 A1 | 12/1999 |
| EP | 0974836 A2 | 1/2000 |
| EP | 0978721 A1 | 2/2000 |
| EP | 1139098 A2 | 10/2001 |
| JP | 2000-241380 | 9/2000 |

OTHER PUBLICATIONS

French Search Report.

* cited by examiner

Primary Examiner—Daniel S. Larkin
(74) Attorney, Agent, or Firm—Nixon & Vanderhye PC

(57) ABSTRACT

An improved structure of a gas sensor is provided which is designed to provide a joint between a gas sensor element protective cover and a sensor housing which is insensitive to heat. The housing has formed on a side wall thereof a thread used to installation of the gas sensor, for example, in an exhaust pipe of automotive engines. The joint is located closer to a base end of the sensor housing than a top end of the thread. Specifically, when the gas sensor is installed in the exhaust pipe of the engine, the joint is located farther away from a heat source (i.e., exhaust gasses of the engine) than the top end of the thread, thereby avoiding loosening of the joint or dislodgement of the cover from the housing.

4 Claims, 10 Drawing Sheets

GAS SENSOR HAVING IMPROVED STRUCTURE FOR INSTALLATION OF PROTECTIVE COVER

BACKGROUND OF THE INVENTION

1. Technical Field of the Invention

The present invention relates generally to a gas sensor which is to be installed in an exhaust pipe of automotive engines to measure the concentration of gas such $O_2$, NOx, or CO, and more particularly to an improved structure of such a gas sensor which is designed to minimize thermal damage to a joint between a housing and a sensor element protective cover placed in a high-temperature atmosphere of exhaust gasses.

2. Background Art

Gas sensors are know which are installed in an exhaust pipe of automotive vehicles for use in air-fuel ratio control of engines.

FIGS. 14 and 15 show one example of such a type of gas sensor which is taught in Japanese Patent First Publication No. 2000-241380 (corresponding to U.S. Pat. No. 6,214,186 B1, issued Apr. 10, 2001, assigned to the same assignee as that of this application).

The gas sensor 9 includes a gas sensor element 19 working to measure the concentration of a given component contained in gasses, a housing 90 within which the gas sensor element 19 is disposed through an insulation porcelain 12, a gas sensor element protective cover assembly 91 joined to a head end of the housing 90, and an atmosphere side cover 2 joined to a base end of the housing 90.

The gas sensor element protective cover assembly 91 is of a double-walled structure consisting of an outer cover 92 and an inner cover 93. The outer and inner covers 92 and 93, as clearly shown in FIG. 15, have flanges 920 and 930 extending outward. The housing 90 has a cover installation groove 903 formed in the head end thereof and an annular extension 902 extending outside a base end surface 901 of the housing 90. Installation of the gas sensor element protective cover assembly 91 on the housing 90 is achieved by placing the flanges 920 and 930 of the outer and inner covers 92 and 93 within the cover installation groove 903 and bending the extension 902 inward to retain the flanges 920 and 930 within the cover installation groove 903.

The housing 90 has formed on an outer wall, as denoted at B in FIG. 15, thereof an external thread 904 which is engageble with an internal thread cut in an inner wall of a sensor mount hole formed in an exhaust pipe of the automotive engine. The housing 90 also has, as shown in FIG. 14, a tapered shoulder 906 formed on an inner side wall 905 which bears the insulation porcelain 12. Specifically, the housing 90 is complex in structure and must be made of material easy to machine.

When the gas sensor 9 is installed in the exhaust pipe of the automotive engine, a lower portion of the gas sensor 9 below a broken line M in FIG. 14 is exposed to the exhaust gasses, so that the gas sensor element protective cover assembly 91 is exposed to intense heat. The gas sensor element protective cover assembly 91, thus, needs to be made of heat resisting material.

Most typical heat resisting materials are difficult to machine. It is, thus, difficult to make the housing 90 with the same heat resisting material as that of the protective gas sensor element protective cover assembly 91. In a case where the housing 90 is made of material different from that of the gas sensor element protective cover assembly 91, they will have coefficients of thermal expansion different from each other, which facilitates loosening of a joint of the gas sensor element protective cover assembly 91 to the housing 90 or dislodgement of the gas sensor element protective cover assembly 91 from the housing 90.

SUMMARY OF THE INVENTION

It is therefore a principal object of the present invention to avoid the disadvantages of the prior art.

It is another object of the present invention to provide an improved structure of a gas sensor which provides a joint between a gas sensor element protective cover and a housing which is insensitive to heat.

According to one aspect of the invention, there is provided a gas sensor which may be installed in an exhaust pipe of automotive engines to measure the concentration of a given component of exhaust gasses of the engine. The gas sensor comprises: (a) a hollow cylindrical housing having a length with a first end and a second end opposed to the first end; (b) a measurement gas side insulation porcelain disposed within the housing; (c) a sensor element disposed within the measurement gas side insulation porcelain, the sensor element having a base portion projecting from the first end of the housing and a sensing portion projecting from the second end of the housing; (d) an atmosphere side cover installed on the first end of the housing; (e) an atmosphere side insulation porcelain disposed on the measurement gas side insulation porcelain within the atmosphere side cover to cover the base portion of the sensor element; (f) a thread formed on a portion of a side wall of the housing on a side of the second end for joint of the gas sensor to a given member to expose the sensing portion of the sensor element to a measurement gas, the thread having a top end close to the second end of the housing; and (g) a measurement side cover joined to the second end of the housing to cover the sensing portion of the sensor element. A joint of the measurement side cover to the second end of the housing is located closer to the first end of the housing than the top end of the thread. Specifically, in a case where the gas sensor is installed in an exhaust pipe of automotive engines, the joint is located farther away from a heat source (i.e., exhaust gasses of the automotive engine) than the top end of the thread use to mount the gas sensor element protective cover in the exhaust pipe, thus resulting in a difficulty in loosening of the joint or dislodgement of the sensor element protective cover from the housing.

In the preferred mode of the invention, the housing has an opening formed in the second end thereof through which the sensing portion of the gas sensor element passes and a cover installation recess in which an open end of the measurement gas side cover is installed.

The gas sensor may further comprise a cover member made of a material identical with that of the housing. The cover is disposed on the open end of the measurement gas side cover to cover the cover installation recess fixedly.

The housing is of a double-walled structure consisting of an outer cylinder and an inner cylinder disposed within the outer cylinder. The outer and inner cylinders may be designed to retain the open end of the measurement gas side cover therebetween.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
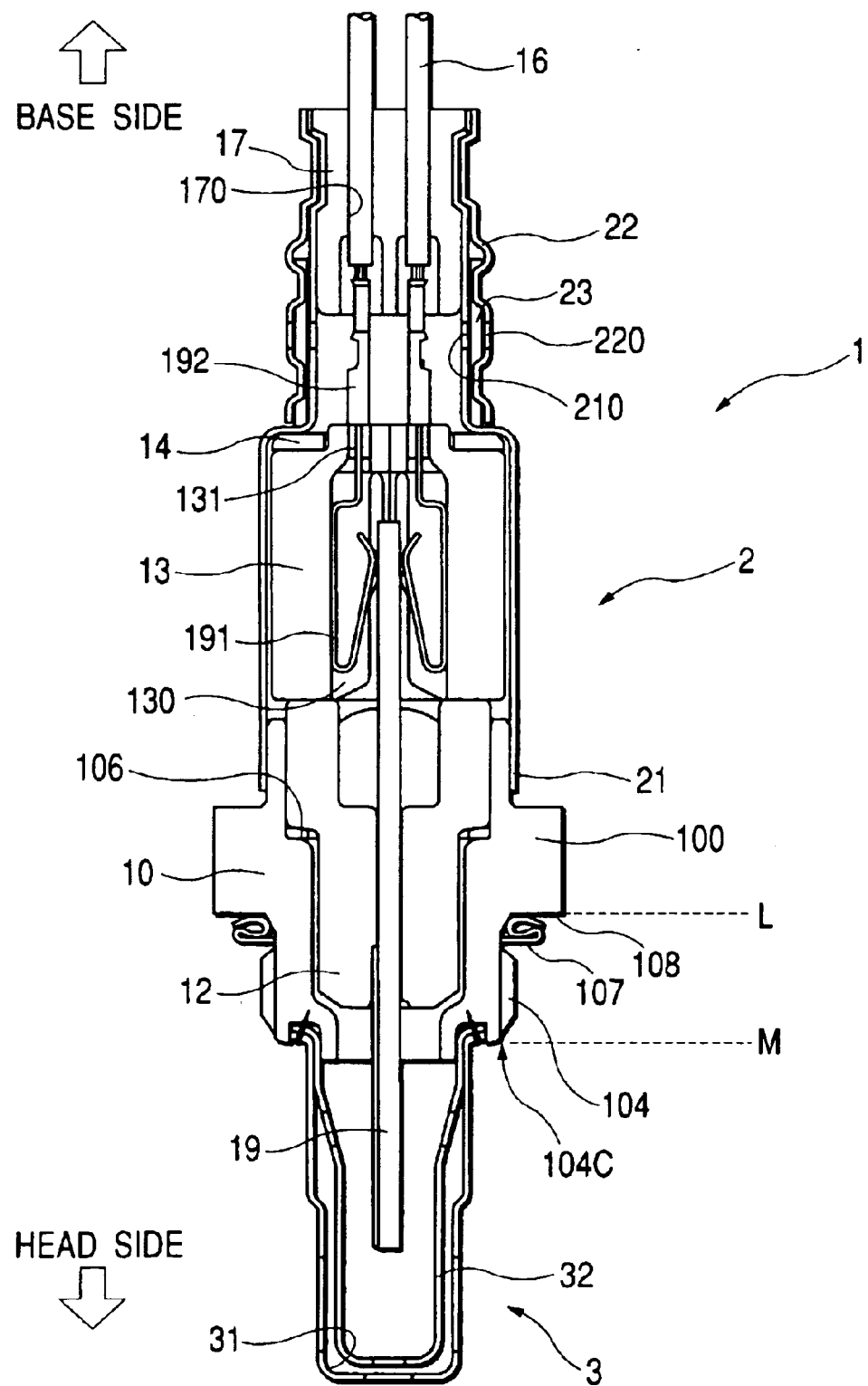
FIG. 1 is a longitudinal sectional view which shows a gas sensor according to the first embodiment of the invention.

Referring now to the drawings, wherein like numbers refer to like parts in several views, particularly to FIG. 1, there is shown a gas sensor 1 according to the first embodiment of the invention which may be employed in automotive air-fuel ratio control systems to measure $O_2$, HC, CO, or NOx contained in exhaust gasses of an internal combustion engine.

The gas sensor 1 generally includes a hollow cylindrical housing 10, an insulation porcelain 12 fitted within the housing 10, a gas sensor element 19 retained within the insulation porcelain 12, a double-walled protective cover assembly 3 secured to a head end of the housing 10 to cover a sensing portion of the gas sensor element 19, an insulation porcelain 13 covering a base portion of the gas sensor element 19, and a hollow cylindrical air cover 2 joined to a base end of the housing 10.

The gas sensor element 19 may be made of a laminated plate such as one taught in U.S. Pat. No. 5,573,650, issued Nov. 12, 1996 to Fukaya et al., the disclosure of which is incorporated herein by reference. The gas sensor element 19 may alternatively be made of a known cup-shaped sensor element.

Figure 2:
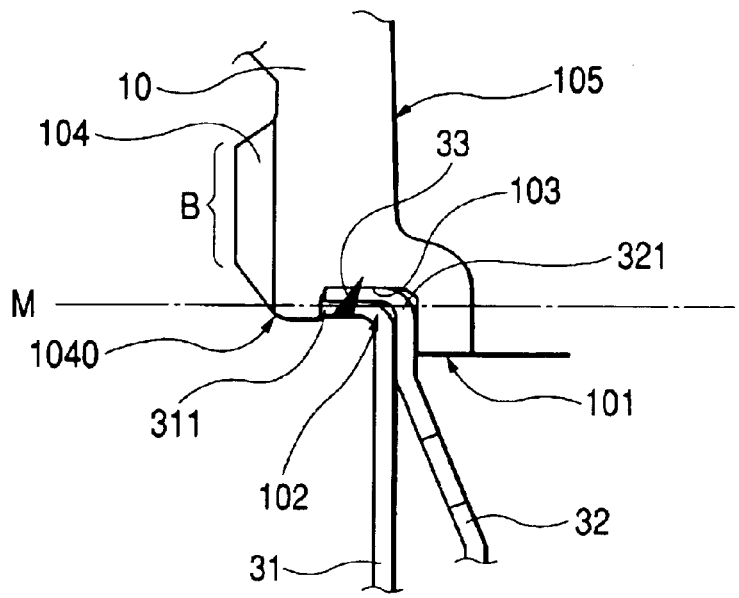
FIG. 2 is a partially enlarged sectional view which shows installation of a cover assembly to a housing in the first embodiment.

The housing 10, as clearly shown in FIG. 2, has formed on an outer wall, as indicated by B, of a head portion thereof an external thread 104 engageble with an internal thread formed in a sensor-mount member, e.g., an exhaust pipe of automotive engines for installation of the gas sensor 1 in the exhaust pipe. A joint of an open end of the protective cover assembly 3 to the head end of the housing 10 is located closer to the base end of the housing 10 than a top end 1040 of the thread 104.

The housing 10 has an opening formed in a head end surface 101 thereof and a cover installation groove 102, as will be described later in detail, to which the open end (also referred to as a base end below) of the protective cover assembly 3 is welded.

The gas sensor 1 is installed, for example, in a wall of the exhaust pipe joining to the automotive engine to determine an air-fuel ratio for use in air-fuel ratio control of the engine. In the installation of the gas sensor 1, an end surface 108 of a flange 100 of the housing 10, as illustrated in FIG. 1, is placed in abutment to an outer surface of the exhaust pipe through a spring 107. The spring 107 works to provide hermetic sealing between the end surface 108 and the outer surface of the exhaust pipe.

When the engine is running, a lower portion of the gas sensor 1 below a broken line M in FIG. 1, is exposed to exhaust gasses flowing within the exhaust pipe and heated thereby. An upper portion of the gas sensor 1 above a broken line L is exposed to the atmospheric air. The temperature of the gas sensor 1, thus, decreases gradually from the broken line L to the base end of the gas sensor 1 (i.e., the upper end, as viewed in FIG. 1).

The housing 10, as described above, has the external thread 104 formed on the head portion beneath the flange 100, as viewed in FIG. 1, for installation of the gas sensor 1 in the exhaust pipe of the engine. The exhaust pipe has formed therein a sensor-mount hole. The sensor-mount hole has formed in an inner side wall thereof an internal thread which is engageble with the external thread 104 of the housing 10 to install the gas sensor 1 in the exhaust pipe fixedly.

The protective cover assembly 3 is of a double-walled structure and made up of an outer cylindrical cover 31 and an inner cylindrical cover 32 disposed within the outer cover 31 coaxially with each other. The outer and inner covers 31 and 32, as shown in FIGS. 1 and 2, have gas holes through which the exhaust gasses pass and enters inside a gas chamber defined in the inner cover 32. The gas sensor 1 has a head portion (i.e., the sensing portion) exposed to the exhaust gasses in the inner cover 32. The protective cover assembly 3 may alternatively be of a single- or multi-walled (more than two) structure.

The outer and inner covers 31 and 32 have open end portions 311 and 321 which are bent or expand outward substantially in a radius direction of the gas sensor 1 perpendicular to a longitudinal center line of the gas sensor 1. The open end portions 311 and 321 will also be referred to below as flanges, respectively.

The housing 10, as described above, has the cover installation groove 102 formed in the head end surface thereof. The installation of the protective cover assembly 3 on the housing 10 is achieved by fitting the flanges 311 and 321 of the outer and inner covers 31 and 32 in the cover installation groove 102 in contact of the flange 321 with a bottom surface 103 of the cover installation groove 102 and welding portions of the flanges 311 and 321 to the bottom surface 103, as indicated at 33 in FIG. 2. The weld 33 (i.e., a contact) between the protective cover assembly 3 and the bottom surface 103 of the cover installation groove 102 is located closer to the base end (i.e., the upper end, as viewed in FIG. 1) of the housing 10 than the top end 1040 of the thread 104.

The housing 10 is made of ferritic stainless steel, such as SUS430, in terms of ease of machining. The outer and inner covers 31 and 32 are made of austenitic stainless steel, such as SUS310, in terms of heat resistance.

The gas sensor element 19 is retained within the housing 10 through the insulation porcelain 12. Gas-tight seals are formed between the insulation porcelain 12 and the housing 10 and between the insulation porcelain 12 and the gas sensor element 19.

The insulation porcelain 13 is disposed within the air cover in alignment with the insulation porcelain 12. The insulation porcelain 13 has formed therein a cavity 130 within which the base portion of the gas sensor element 19 is disposed. The insulation porcelain 13 has formed in a base end thereof holes 131 leading to the cavity 130.

The gas sensor element 19 connects with leads 16 through terminals 191 and connectors 192, such as clamp contacts, for transmitting an output of the gas sensor element 19 to and receiving electric power from an external sensor controller (not shown). The terminals 191 pass through the holes 131 and extend into an air chamber formed inside a base portion of the air cover 2 above the insulation porcelain 13. Within the air chamber, the terminals 191 are joined electrically to the leads 16 through the connectors 192.

An elastic sealing member 17 is fitted within an opening of the air cover 2. The leads 16 extend through holes 170 formed in the sealing member 17.

A disc spring 14 is placed on the base end of the insulation porcelain 13. The disc spring 14 has a configuration which produces a spring pressure when the insulation porcelain 13 is pressed against a shoulder of the air cover 2.

The insulation porcelain 12 is disposed within the housing 10, as clearly shown in FIG. 1, in contact with a tapered shoulder 106 through a seal. The insulation porcelain 13 is placed in abutment to the base end of the insulation porcelain 12. The disc spring 14 is so disposed between the base end of the insulation porcelain 13 and an inner surface of a shoulder of the air cover 2 as to produce the spring pressure urging the insulation porcelain 13 into constant abutment with the shoulder 106 of the housing 10 to form a hermetic sealing therebetween.

The air cover 2 is made up of a cylindrical main cover 21 and a cylindrical filter cover 22. The main cover 21 is welded directly to a side wall of the base portion of the housing 10. The filter cover 22 is secured to an outer surface of a small-diameter portion of the main cover 21 and crimped to retain a water-repellent filter 23 on the periphery of the main cover 21. The main cover 21 and the filter cover 22 have formed therein air vents 210 and 220 through which air is admitted into the air chamber defined inside the small-diameter portion of the main cover 21. The air vents 210 and 220 face the water-repellent filter 23.

As described above, the weld 33 of the protective cover assembly 3 to the housing 10 (i.e., an interface between the flange 321 of the inner cover 32 and the bottom surface 103 of the cover installation groove 102) is located away from the top end 1040 of the thread 104 toward the base portion of the housing 10. During usage, the gas sensor 1 is exposed to high-temperature exhaust gases of the engine, so that the protective cover assembly 3 is heated up. A portion of the gas sensor 1 exposed directly to the exhaust gasses is between the top end 1040 of the thread 104 and the head of the gas sensor 1. The remaining portion of the gas sensor 1, therefore, is not exposed to the exhaust gasses or a heat source, so that the temperature thereof decreases toward the base end. The location of the weld 33 of the protective cover assembly 3 to the housing 10 closer to the base end of the housing 10 than the top end 1040 of the thread 104 serves to minimize physical damage to the weld 33, that is, dislodgement of the protective cover assembly 3 from the housing 10 due to a difference in coefficient of thermal expansion between the protective cover assembly 3 and the housing 10, which are made of different materials.

The weld 33 provides a joint between the protective cover assembly 3 and the housing 10 which is mechanically stronger than would be the case where an edge of the housing 10 is crimped to retain the flanges 311 and 321 of the protective cover assembly 3 within the cover installation groove 102 of the housing 10. The use of the cover installation groove 102 facilitates ease of positioning of the protective cover assembly 3 (i.e., the flanges 311 and 321 of the outer and inner covers 31 and 32) relative to the housing 10, thereby ensuring the location of the weld 33 (i.e., the interface between the inner cover 32 and the bottom surface 103 of the cover installation groove 102) farther away from the heat source (i.e., the exhaust gasses of the engine) than the top end 1040 of the thread 104.

Figure 3:
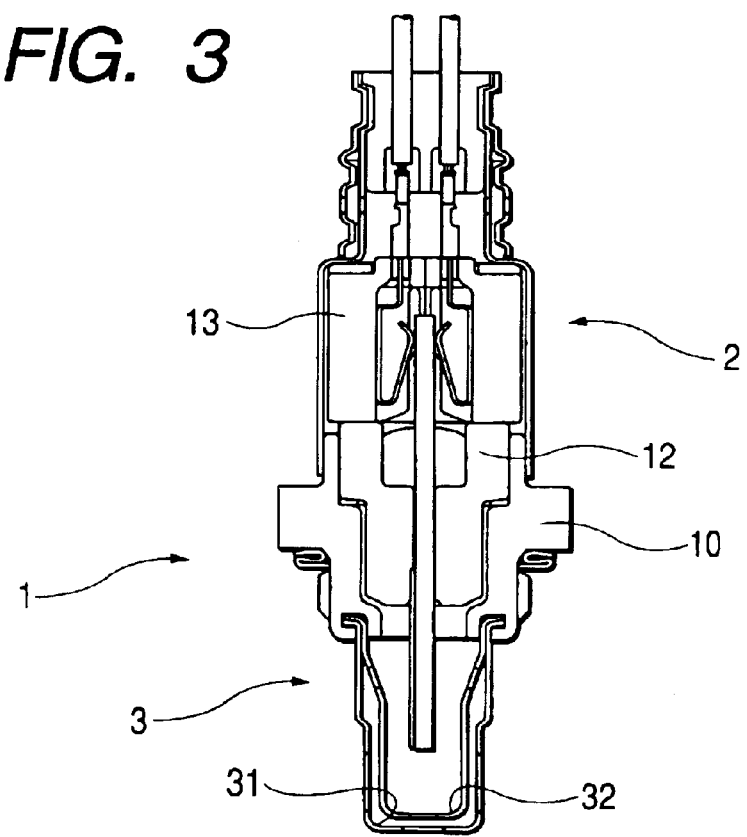
FIG. 3 is a longitudinal sectional view which shows a gas sensor according to the second embodiment of the invention.
Figure 4A:
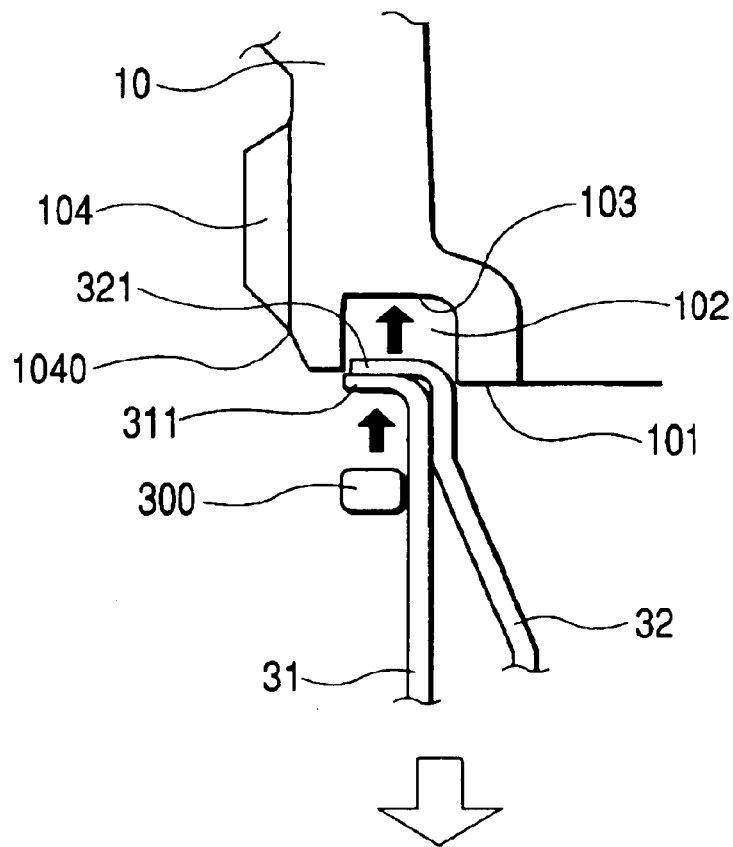
FIGS. 4(a) and 4(b) are partially enlarged sectional views which show steps of installing a cover assembly to a housing in the second embodiment.
Figure 4B:
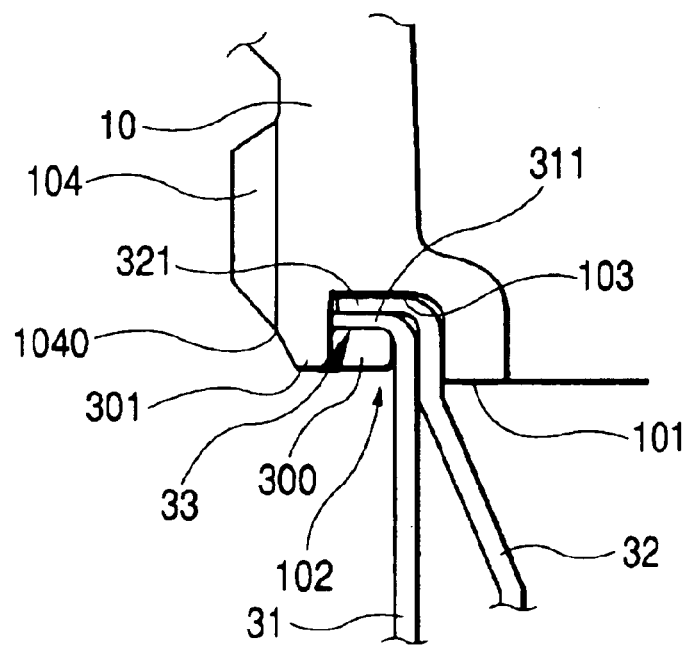

FIGS. 3, 4(a), and 4(b) show the gas senor 1 according to the second embodiment of the invention.

The gas sensor 1 includes, as clearly shown in FIGS. 4(a) and 4(b), an annular cover 300 made of the same material as that of the housing 10. For instance, the housing 10 and the annular cover 300 are made of stainless steel, such as SUS430, in terms of machineability. The outer and inner covers 31 and 32 are made of stainless steel, such as SUS310, in terms of heat resistance. The annular cover 300 is substantially identical in configuration with the cover installation groove 102. The outer and inner covers 31 and 32 are identical in structure with those in the first embodiment. The housing 10 is identical in structure with that in the first embodiment except that the depth of the cover installation groove 102 is greater than that in the first embodiment.

In installation of the protective cover assembly 3 on the housing 3, the flanges 311 and 321 of the outer and inner covers 31 and 32 are first disposed within the cover installation groove 102 into abutment of the flange 321 with the bottom surface 103. Next, the annular cover 300 is, as clearly shown in FIG. 4(a), placed within the cover installation groove 102 into abutment with the surface of the flange 311 of the outer cover 31 and an outer inner wall of the cover installation groove 102, as shown in FIG. 4(b), to substantially close the cover installation groove 102, that is, to retain the flange 311 within the cover installation groove 102. Finally, an inner edge of an outer wall 301 of the cover installation groove 102 is, as shown in FIG. 4(b), welded to the annular cover 300 in a direction toward the bottom surface 103 of the cover installation groove 102, thereby retaining the flanges 311 and 321 within the cover installation groove 102.

The weld 33 between the housing 10 and the annular cover 300 is, as can be seen from FIG. 4(b), located closer to the head of the gas sensor 1 than the top end 1040 of the thread 104, but however, the annular cover 300 urges the flanges 311 and 321 into constant abutment with the bottom surface 103 of the cover installation groove 102, so that an interface between the flange 321 of the inner cover 32 and the bottom surface 103 is located closer to the base end of the gas sensor 1 than the top end 1040 of the thread 104.

The housing 10 and the annular cover 300 are, as described above, made of the same material and thus have coefficients of thermal expansion identical with each other. This eliminates the dislodgement of the outer and inner covers 31 and 32 from the housing 10 due to a difference in coefficient of thermal expansion between the housing 10 and the protective cover assembly 3.

Figure 5:
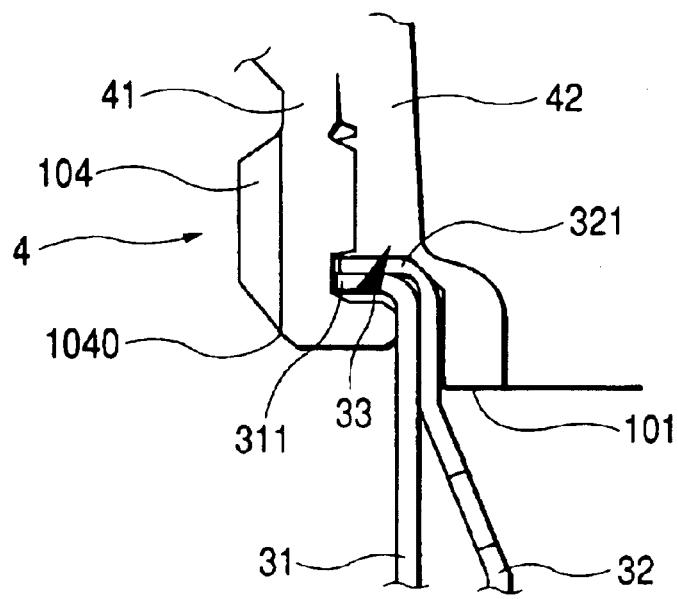
FIG. 5 is a partially enlarged sectional view which shows installation of a cover assembly to a housing according to the third embodiment of the invention.
Figure 6:
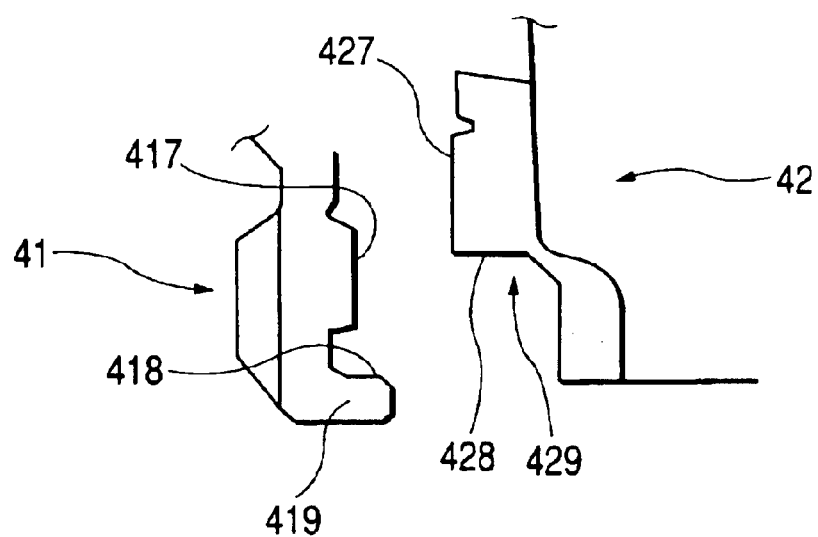
FIG. 6 is a partially exploded sectional view which shows a structure of a housing in the third embodiment.
Figure 7:
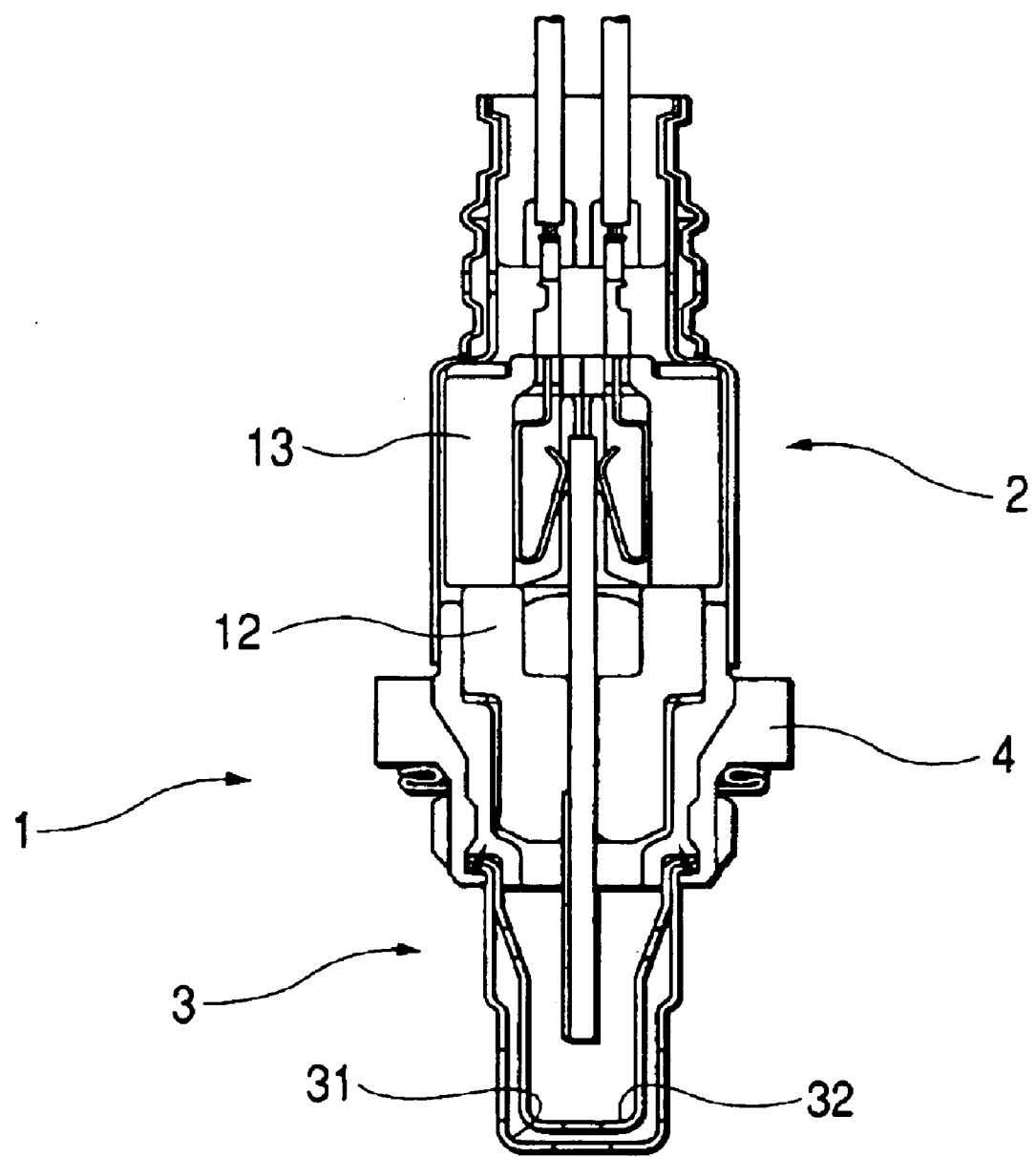
FIG. 7 is a longitudinal sectional view which shows a gas sensor in third embodiment of the invention.

FIGS. 5, 6, and 7 show the gas sensor 1 according to the third embodiment of the invention.

The gas senor 1, as shown in FIG. 7, includes a housing 4. The housing 4 is, as shown in FIGS. 5 and 6, made up of an outer cylinder 41 and an inner cylinder 42 fitted within the outer cylinder 41 and retains the protective cover assembly 3 between the outer and inner cylinders 41 and 42.

The housing 4 is made of stainless steel, such as SUS430, in terms of machineability. The outer and inner covers 31 and 32 are made of stainless steel such as SUS310 in terms of heat resistance.

The inner cylinder 42, as clearly shown in FIGS. 5 and 6, has an annular shoulder 429. The outer cylinder 41 has an annular protrusion 419 extending inwardly from a top end thereof. The inner cylinder 42 also has a thread 427 formed in an outer side wall just above the shoulder 429. Similarly, the outer cylinder 41 has formed in an inner side wall above the annular protrusion 419 a thread 417 which engages the thread 427 of the inner cylinder 42 to define a cover installation groove between a surface 428 of the shoulder 429 and the surface 418 of the annular protrusion 419. The surface 428 may extend parallel to the surface 418.

Installation of the protective cover assembly 3 on the housing 4 is accomplished by welding the flanges 311 and 321 of the outer and inner covers 31 and 32 to the surface 428 of the shoulder 429 of the inner cylinder 42, placing the annular protrusion 419 beneath the shoulder 429, as viewed in the drawings, in alignment of the outer cylinder 41 with the inner cylinder 42, and turning the outer and inner cylinders 41 and 42 relative to each other to bring the threads 417 and 427 into engagement with each other to retain the flanges 311 and 321 within the cover installation groove firmly.

The weld 33 between the flanges 311 and 321 of the outer and inner covers 31 and 32 and the inner cylinder 42 is, as clearly shown in FIG. 5, located closer to the base end of the housing 4 than the top end 1040 of the thread 104, like the first embodiment.

Other arrangements are identical with those in the first embodiment, and explanation thereof in detail will be omitted here.

Figure 8:
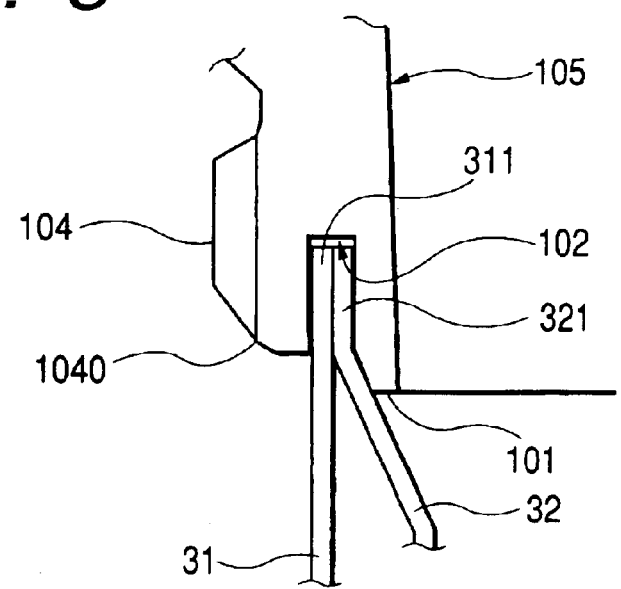
FIG. 8 is a partially enlarged sectional view which shows installation of a cover assembly to a housing according to the fourth embodiment of the invention.
Figure 9:
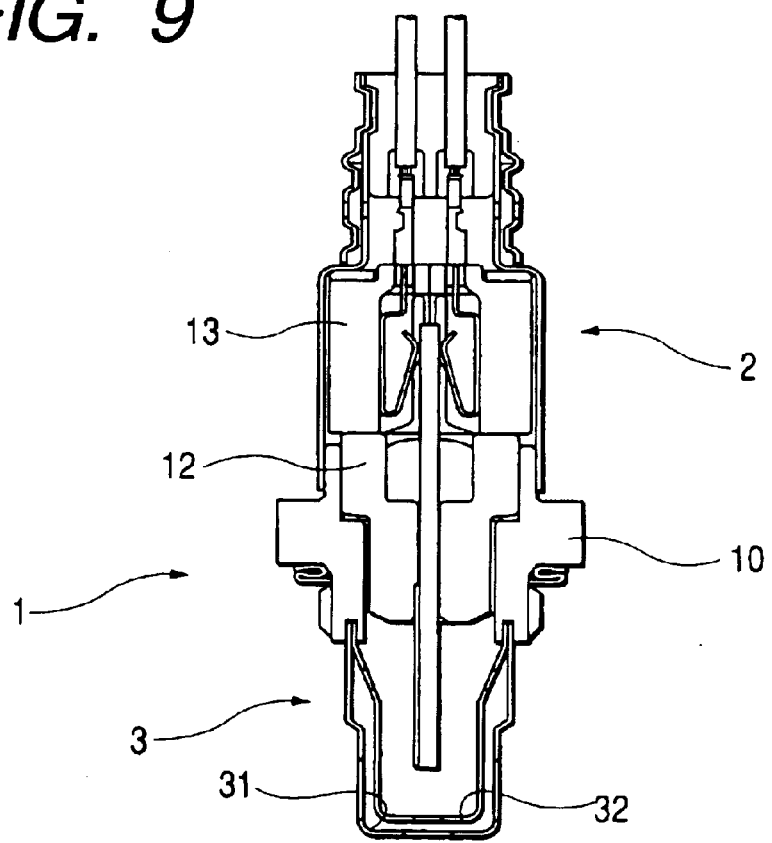
FIG. 9 is a longitudinal sectional view which shows a gas sensor in the fourth embodiment of the invention.

FIGS. 8 and 9 show the gas sensor 1 according to the fourth embodiment of the invention.

The housing 10 has formed in the head end surface 101 thereof the cover installation groove 102 which is deeper than that in the first embodiment. Specifically, the width of the cover installation groove 102 is smaller than the depth thereof.

The housing 10 is made of stainless steel, such as SUS430, in terms of machineability. The outer and inner covers 31 and 32 of the protective cover assembly 3 are made of stainless steel, such as SUS310, in terms of heat resistance.

The outer cover 31 has the open end portion 311 extending straight. The inner cover 32 has the open end portion 321 extending parallel to the open end portion 311 of the outer cover 31. The width of the cover installation groove 102 is slightly smaller than a total thickness of the open end portions 311 and 321 in order to provide a press fit of the open end portions 311 and 321 within the cover installation groove 102 to retain the protective cover assembly 3 firmly on the housing 10.

A joint between the outer and inner covers 31 and 32 and the housing 10 is, like the first embodiment, located closer to the base end of the housing 10 than the top end 1040 of the thread 104. Other arrangements are identical with those in the first embodiment, and explanation thereof in detail will be omitted here.

Figure 10:
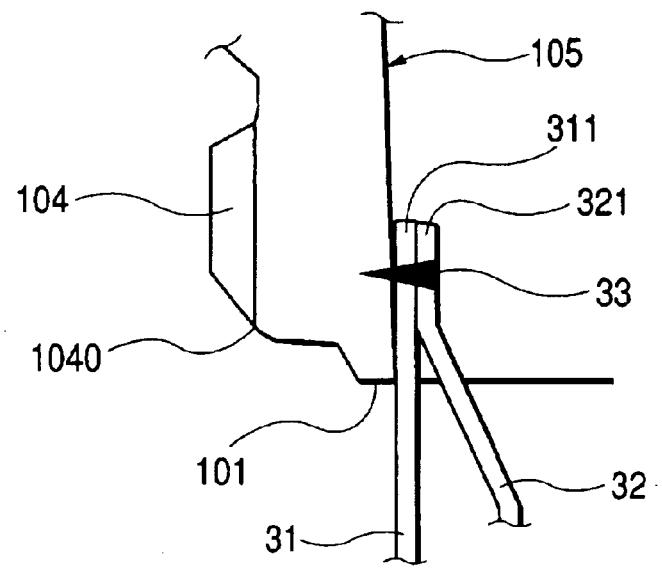
FIG. 10 is a partially enlarged sectional view which shows installation of a cover assembly to a housing according to the fifth embodiment of the invention.
Figure 11:
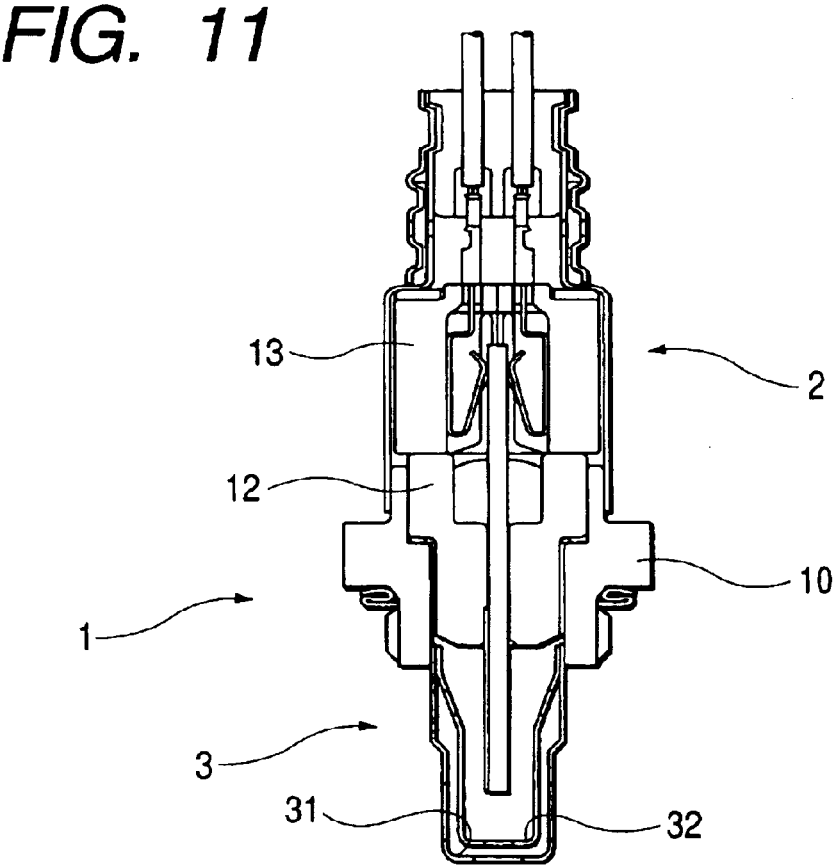
FIG. 11 is a longitudinal sectional view which shows a gas sensor in the fifth embodiment of the invention.

FIGS. 10 and 11 show the gas sensor 1 according to the fifth embodiment of the invention.

The housing 10 is like the above embodiments, made of steel, such as SUS430, in terms of machineability. The outer and inner covers 31 and 32 of the protective cover assembly 3 are made of stainless steel, such as SUS310, in terms of heat resistance.

The outer and inner covers 31 and 32, like the fourth embodiment, the open end portions 311 and 321 extending parallel to each other in a longitudinal direction of the housing 10.

Installation of the protective cover assembly 3 on the housing 10 is accomplished by placing the open end portions 311 and 321 of the outer and inner covers 31 and 32 within the housing 10 in abutment to the inner wall 105 of the housing 10 and welding the open end portions 311 and 321 to the inner wall 105. The weld 33 between the open end portions 311 and 321 and the inner wall 105 is, like the first embodiment, located closer to the base end of the housing 10 than the top end 1040 of the thread 104. Other arrangements are identical with those in the first embodiment, and explanation thereof in detail will be omitted here.

Figure 12:
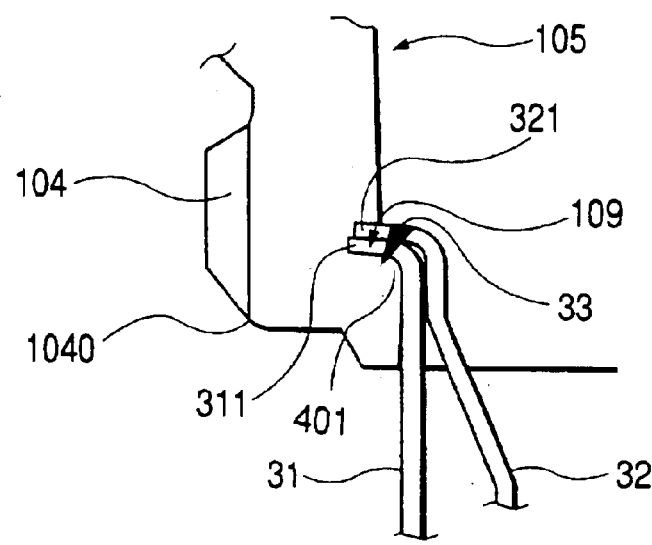
FIG. 12 is a partially enlarged sectional view which shows installation of a cover assembly to a housing according to the sixth embodiment of the invention.
Figure 13:
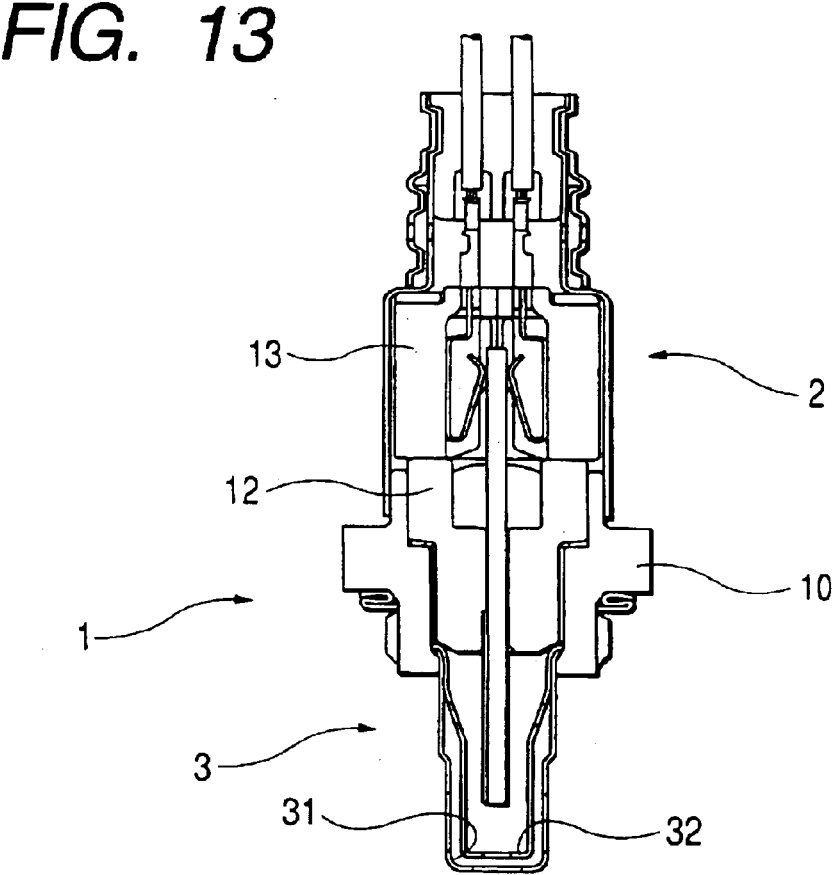
FIG. 13 is a longitudinal sectional view which shows a gas sensor in the sixth embodiment of the invention.
Figure 14:
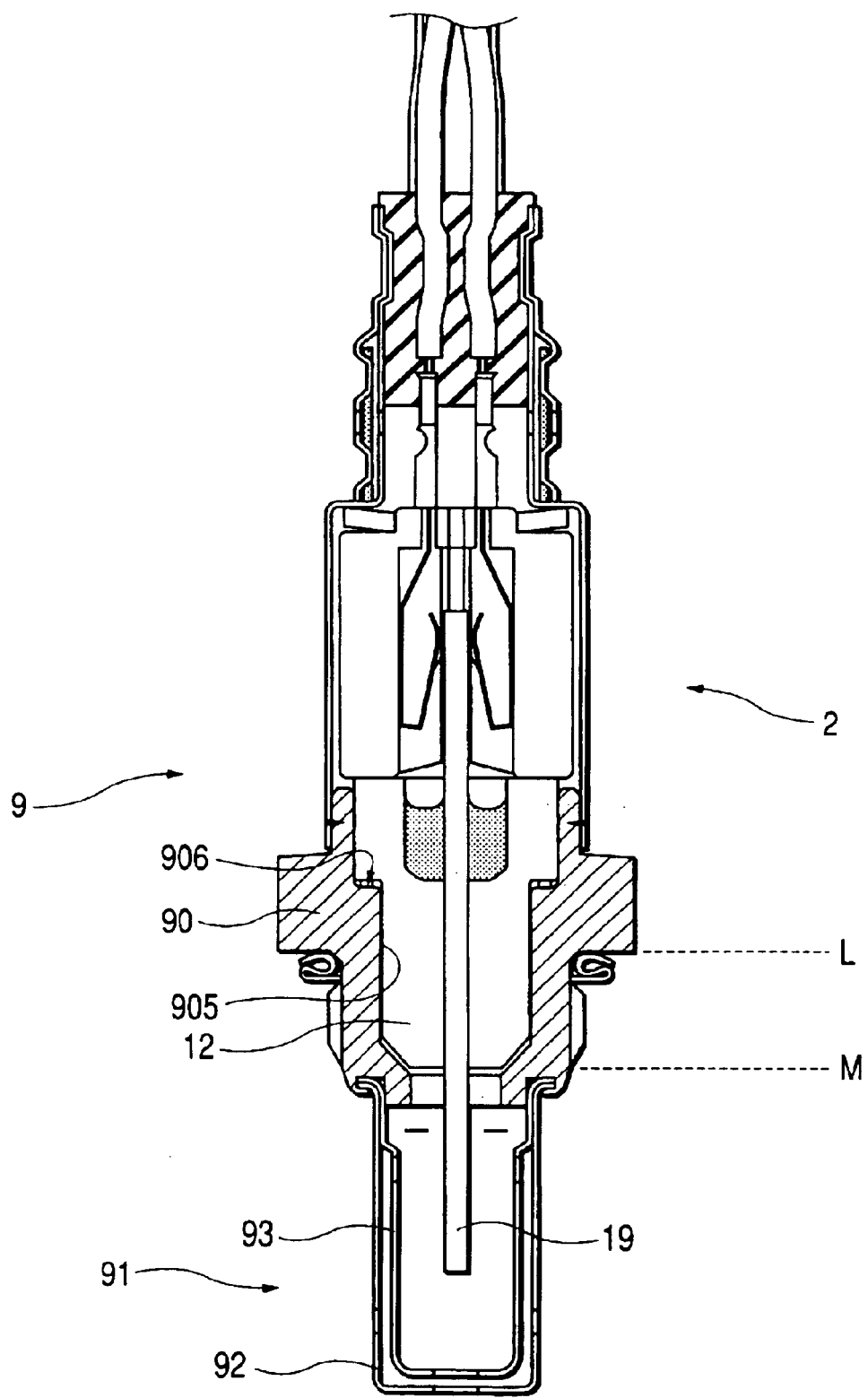
FIG. 14 is a longitudinal sectional view which shows a conventional gas sensor.
Figure 15:
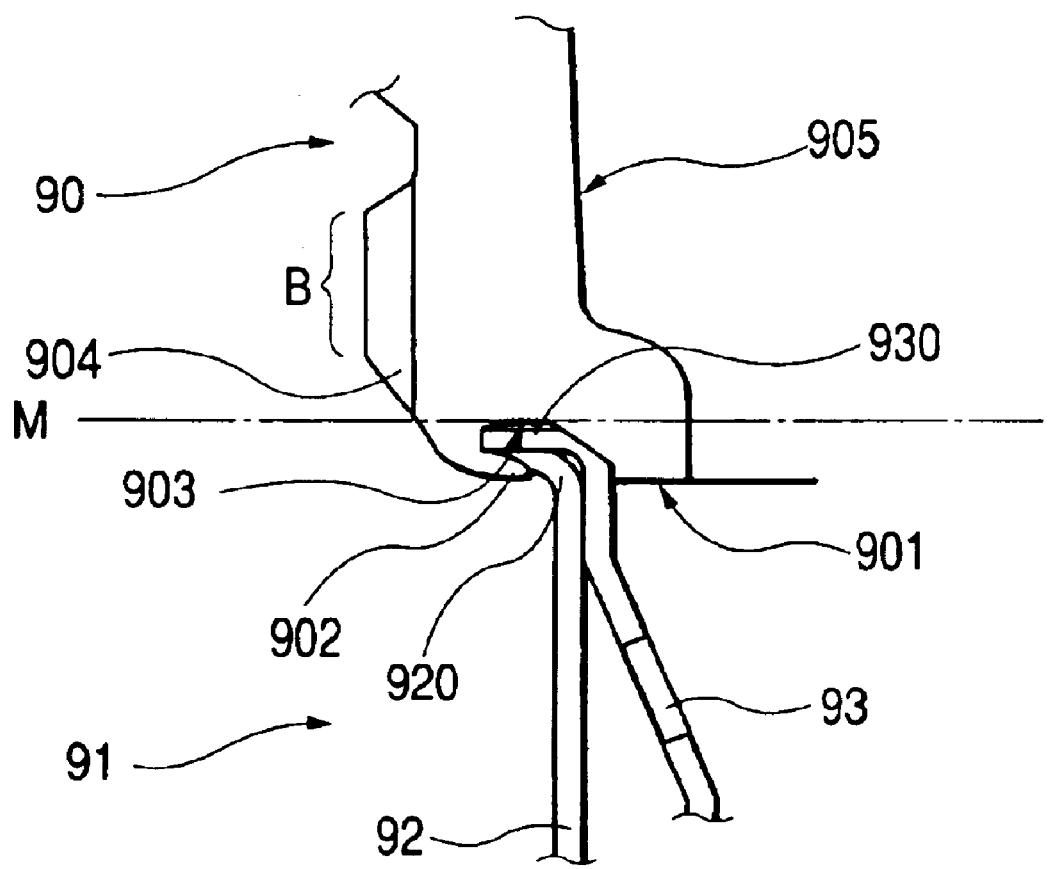
FIG. 15 is a partially enlarged sectional view which shows installation of a cover assembly to a housing of the gas sensor as illustrated in FIG. 14.

FIGS. 12 and 13 show the gas sensor 1 according to the sixth embodiment of the invention.

The housing 10 is, like the above embodiments, made of stainless steel such as SUS430 in terms of machineability. The outer and inner covers 31 and 32 of the protective cover assembly 3 are made of stainless steel such as SUS310 in terms of heat resistance.

The outer and inner covers 31 and 32 of the protective cover assembly 3 have, like the first embodiment, the flanges 311 and 321 extending outward substantially in the radius direction of the protective cover assembly 3. The housing 10 has, as clearly shown in FIG. 12, has an inner shoulder 401 and an annular cover installation groove 109 formed in the inner wall 105 just above the shoulder 401. The cover installation groove 109 substantially faces the middle of the thread 104 in the longitudinal direction of the housing 10. The shoulder 401 is contoured to conform with the contour of the flange 311 of the outer cover 31.

Installation of the protective cover assembly 3 on the housing 10 is accomplished by inserting the flanges 311 and 321 into the cover installation groove 109 and welding the flanges 311 and 321 of the outer and inner covers 31 and 32 to the shoulder 401 in a direction from the inner surface of the flange 321 (i.e., an upper surface, as viewed in FIG. 12) toward a corner of the shoulder 401. The weld 33 between the flanges 311 and 321 and the housing 10 is, like the first embodiment, located closer to the base end of the housing 10 than the top end 1040 of the thread 104. Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor comprising:
   a hollow cylindrical housing having a length with a first end and a second end opposed to the first end;
   a measurement gas side insulation porcelain disposed within said housing;
   a sensor element disposed within said measurement gas side insulation porcelain, said sensor element having a base portion projecting from the first end of said housing and a sensing portion projecting from the second end of said housing;
   an atmosphere side cover installed on the first end of said housing;
   an atmosphere side insulation porcelain disposed on said measurement gas side insulation porcelain within said atmosphere side cover to cover the base portion of said sensor element;
   a thread formed on a portion of a side wall of said housing on a side of said second end for joint of said gas sensor to a given member to expose the sensing portion of said sensor element to a measurement gas, said thread having a top end closer to said second end of said housing than to the first end; and
   a measurement side cover welded to the second end of said housing to cover the sensing portion of said sensor element, weld of said measurement side cover to said second end of said housing being located closer to the first end of said housing than the top end of said thread.

2. A gas sensor as set forth in claim 1, wherein said housing has an opening formed in the second end thereof and a cover installation recess in which an open end of said measurement side cover is installed.

3. A gas sensor as set forth in claim 2, further comprising a cover member made of a material identical with that of said housing, said cover member is disposed on the open end of said measurement side cover to cover said cover installation recess fixedly.

4. A gas sensor as set forth in claim 2, wherein said housing is of a double-walled structure consisting of an outer cylinder and an inner cylinder disposed within the outer cylinder, the outer and inner cylinders retaining the open end of said measurement side cover therebetween.

* * * * *